United States Patent [19]

Hoving et al.

[11] Patent Number: 4,578,372

[45] Date of Patent: Mar. 25, 1986

[54] PREPARATION OF ZEOLITE COATED SUBSTRATES

[75] Inventors: Klaas Hoving, Heenvliet; Johannes W. M. Walterbos, Hellevoetsluis, both of Netherlands

[73] Assignee: Exxon Research & Engineering Co., Florham Park, N.J.

[21] Appl. No.: 683,366

[22] Filed: Dec. 19, 1984

[30] Foreign Application Priority Data

Dec. 30, 1983 [GB] United Kingdom ................ 8334626

[51] Int. Cl.$^4$ .................... B01J 29/06; B01J 37/00; B22F 5/00
[52] U.S. Cl. .................................. 502/74; 502/60; 502/66; 502/69; 252/62.55
[58] Field of Search ............... 502/60, 64, 69, 8, 10, 502/66, 74; 252/62.51, 62.55

[56] References Cited

U.S. PATENT DOCUMENTS

| | | | |
|---|---|---|---|
| 3,320,170 | 5/1967 | Vickery et al. | 252/62.51 R |
| 3,730,910 | 5/1973 | Albers et al. | 502/69 X |
| 4,252,679 | 2/1981 | Mertzweiller et al. | 252/62.55 X |

*Primary Examiner*—Carl F. Dees
*Attorney, Agent, or Firm*—M. D. Bittman; J. J. Mahon

[57] ABSTRACT

There is disclosed a process for preparing magnetizable particles comprising Zeolite Y wherein magnetizable particles are introduced into a vessel containing the reaction mixture used to form Zeolite Y and, during heating, the vessel is rotated so that the Zeolite Y is formed as a layer on the surface of the magnetizable particles.

15 Claims, No Drawings

PREPARATION OF ZEOLITE COATED SUBSTRATES

This invention relates to the preparation of zeolite-coated substrates which may be used as catalysts or adsorbents, and particularly to the preparation of magnetizable zeolite compositions useful in forming fluidized beds of magnetically stabilized particles.

There are many applications where it is useful to have a zeolite deposited on a substrate to improve surface area to weight ratio of the zeolite or to provide strength or a particular form.

GB No. 1 245 349 discloses extended zeolite structures in which extended supports are coated first with a layer of hydrated alumina which is then reacted to form a zeolite thereon.

U.S. Pat. No. 3,730,920 discloses a method for producing zeolite surfaced substrates (particularly inorganic oxides such as silicon oxides and aluminium oxides) by contacting the substrate with aluminiosilicate or with a zeolite yielding mixture. Contact between the substrate and a zeolite yielding mixture is effected by stirring.

EP No. 0 055 044 describes a catalyst composition comprising a crystalline modified-silica zeolite overlying a silica core with the same crystalline structure as the zeolite. These compositions are prepared by introducing performed particles of silica into a synthesis gel for the zeolite so that the zeolite forms on the silica particles. GB No. 2 097 374 describes a particulate crystalline material comprising a core of intermediate pore size crystalline silicate within an outer shell with the same crystal structure and comprising an aluminosilicate. There is no indication within these documents of how a zeolite layer may be formed on a substrate which does not have the same crystal structure as the zeolite.

GB No. 1 567 948 describes the use of zeolite seeds in the preparation of aluminosilicates of the ZSM-5 family in which the a reaction mixture for forming the zeolite and the seeds are heated to bring about the formation of the ZSM-5 zeolite. The reaction mixture may be stirred. EP No. 0 002 960 describes the seeding of a reaction mixture for forming zeolite A with preformed zeolite A. Seeding as such is a well-known technique for initiating crystallization but is not regarded as a means for forming a crystalline layer upon a substrate. Indeed, GB No. 1 567 948 makes it clear that when the seeds used in the described process do not have the ZSM-5 structure the product is a ZSM-5 zeolite and there is no disclosure of any composite product.

GB No. 1 124 524 describes a granulation technique in which preformed zeolite particles are formed into granulates with inorganic binding agents, in which technique zeolite particles and powdered binding agent are agglomerated with water in a rotating vessel, preferably with an oblique axis of rotation, to form granules, which are built up layerwise to 0.2 to 10 mm in diameter. This is a process for forming agglomerates of a large number of zeolite and binder particles from preformed zeolites and gives no direction to the formation of zeolite layers on the surface of discrete substrate bodies. EP No. 0 021 267 describes a similar granulation technique for use in preparing detergent granules.

Zeolites are particularly useful in adsorption processes, and it has now been found that a highly effective adsorbent particle for use in magnetically stabilized fluidized beds may be prepared by forming a zeolite around a magnetizable core, preferably so that the zeolite substantially covers the core, and that the resulting particle has a number of advantages over conventional magnetizable composites containing zeolites.

It is known that a fluidized bed of magnetizable particulate solids can be subjected to a magnetic field and stabilized, and that such a bed is useful in processes requiring fluid-solid contact.

In magnetically stabilized bed processes, like conventional fluidized processes, a fluid is injected upwardly at velocities sufficient to overcome the free fall velocities of the individual particles (due to gravity) and cause bed expansion and fluidization of the particles without sweeping significant amounts of the particles from the bed. In conventional fluidized processes, however, the injection of fluid at velocity sufficient to produce expansion of the bed (i.e., transform the fixed packed bed to a fluidized bed) is accompanied by significant bubble formation whereas, in contrast, in a fluidized bed subjected to the influence of a magnetic field there is an interim, or quiescent state wherein there is little, if any, motion exhibited by the particles within the fluidized bed. Within the magnetically stabilized bed the formation of bubbles (with gas) or chaunds (with a liquid) is virtually eliminated and backmixing is suppressed allowing staging to be achieved. For this reason, magnetically stabilized bed processes offer advantages over both fixed and conventional fluidized bed operations. They are superior to conventional fluidized bed operations in that they provide better counter-current contacting, low fluid and solids back mixing, and lower particle attrition. They are superior to fixed bed operations in that they provide lower pressure drop, better ability to transfer solids, and virtually eliminate bed plugging problems. A process disclosing a magnetically stabilized bed and its mode of operation for conducting catalytic reactions, and the capture of particulates to provide a filtering action is disclosed in U.S. Pat. No. 4,115,927.

In much of the early work on catalytic processes the ferromagnetic component constituted essentially the whole of the particles in the bed. Compositions were also developed comprising ferromagnetic inclusions dispersed within matrices constituted in part of non-ferromagnetic materials and processes for the subjection of beds of such particles to the influence of a magnetic field are known.

U.S. Pat. No. 4,247,987 discloses forming a composite of a magnetizable component and adsorbent (e.g. zeolite) by admixing them with a base for the adsorbent (e.g. silica or alumina) to form a gel which is dried, calcined and sized. U.S. Pat. No. 4,252,679 discloses contacting a magnetic alloy of iron or cobalt with a phosphate ion containing solution to form a film thereon, then admixing with an inorganic oxide matrix, followed by contacting with a noble metal. The composite can be formed by cogellation of the magnetic alloy particles with an inorganic oxide support material (e.g. zeolite) preferably by admixture in a slurry with an inorganic oxide precursor which is precipitated from solution with the magnetic alloy particles. U.S. Pat. No. 4,255,289 discloses an inorganic oxide particulate admixed with magnetic alloy particles and an inorganic precursor which serves as a binder. U.S. Pat. No. 4,289,655 discloses a magnetic iron precursor (illmenite, $FeTiO_3$) incorporated within an inorganic oxide and heated in a reducing atmosphere to form reduced iron metal dispersed throughout the composite.

This invention concerns an improved process for forming zeolite layers on substrates which is particularly useful in forming zeolite coatings on magnetizable particles.

In one aspect this invention provides a process for the preparation of a zeolite layer upon a substrate which does not have the same crystalline structure as the zeolite, in which process the substrate is contacted with a reaction mixture for forming a zeolite and the reaction mixture is heated to bring about zeolite formation, in which the substrate is tumbled within the reaction mixture during heating so as to cause zeolite formation preferentially as a layer on the surface of the substrate.

The invention enables the zeolite to be formed as a layer on the substrate in preference to it being formed as pure zeolite particles within the body of the reaction mixture. It is believed that the mixing technique employed results in the preferential formation of nucleation centres upon the substrate surface rather than within the reaction mixture. Moreover, the product of the process of the invention comprises discrete substrate bodies coated with zeolite rather than agglomerates of separate zeolite particles with substrate bodies.

An important feature of the invention comprises tumbling the substrate within the reaction mixture during heating—that is to say, causing the substrate to be raised and then allowed to fall through the reaction mixture under gravity. This tumbling action is preferably achieved by introducing the substrate and the reaction mixture into a rotatable vessel having an axis inclined to the vertical and rotating the vessel during at least a part of the time that the reaction mixture is heated so as to bring about formation of zeolite in the substrate.

The particular zeolite chosen will depend upon the adsorption or separation which it is to be carried out using the magnetically stabilized fluidized bed. For example, when it is desired to separate aromatic hydrocarbons, specifically of paraxylene or paraxylene and ethylbenzene from $C_8$ aromatic isomeric feedstreams (which may comprise principally ethylbenzene, paraxylene, orthoxylene, and metaxylene), this may be carried out by utilizing zeolites whose internal pore surfaces are accessible for selective combination of solid and solute. Examples of suitable zeolites include potassium substituted zeolite X or Y (synthetic forms of faujasite), barium substituted zeolite X or Y and rubidium substituted zeolite X. Potassium-substituted zeolite Y is particularly preferred.

The preparation of such zeolite adsorbent is well known—for example, potassium-substituted zeolite Y (for convenience referred to as "potassium-Y" or "K-Y") may be synthesized from Na, K-aluminosilicate gels or manufactured by a relatively simple ion exchange with a potassium salt carried out on commercially available sodium-Y-faujasite (Na-Y). Na-Y may in turn be prepared for example as described in U.S. Pat. Nos. 3,130,007, 4,178,352 and 4,175,059. For the preferred separation of aromatic hydrocarbons the faujasite preferably has a silica to alumina ratio ($SiO_2/Al_2O_3$) of less than about 5:1, and preferably about 3.8–4.9:1 (higher ratios are normally detrimental to the separation of paraxylene from other $C_8$ isomers). Potassium-Y-faujasite has been found to be an exceptional adsorbent for separating the xylene isomers; paraxylene being selectivly adsorbed in the presence of metalxylene, orthoxylene, and ethylbenzene. The observed order of sorbability for xylene isomers on potassium-Y-faujasite is paraxylene>ethylbenzene>metaxylene>orthoxylene.

Other adsorbent zeolites may be desirable where different molecules are to be adsorbed, and as used herein the term "zeolites" includes not only aluminosilicate forms, but also low aluminium or substantially aluminium-free silicates with a zeolite structure and analogues of aluminosilicates in which the tetrahedrally coordinated aluminium in the zeolite structure is replaced by one or more elements such as gallium, boron or iron. The preparation of individual zeolites may vary, but in general comprises preparation of a reaction mixture containing a source of silicon, a source of cations and, unless a substantially pure silica form is required, a source of modifying element (typically aluminium as described hereinbefore, but alternatively a source of an element such as boron, gallium or iron). This reaction mixture is then held under appropriate crystallization conditions until the desired zeolite is formed, which may thereafter be modified by subsequent chemical treatment such as ion exchange. The particular synthesis techniques to be employed, including the use of additonal template molecules, particular cations or anions, reaction temperatures and pressures are well documented for each known zeolite. The invention will be described in terms of zeolite Y but it is believed to be within the competence of one skilled in the art to adapt the technique to preparing magnetizable forms of other zeolites, e.g. zeolite A, L, mordenite, omega or ZSM-5.

In a preferred aspect of the invention there is provided a process for the preparation of magnetizable adsorbant particles comprising zeolite Y.

As indicated hereinbefore, the preparation of Zeolite Y is well described in the literature, and it is believed to be within the competence of one skilled in the art to prepare a reaction mixture for forming zeolite Y. According to the invention the magnetizable particles may be introduced into such reaction mixtures so that zeolite Y is formed therearound.

By way of illustration, preferred reaction mixtures comprise reactants in the following molar ratios (expressed in terms of oxides):

|  |  | Preferred | Highly Preferred |
|---|---|---|---|
| $Na_2O/SiO_2$ | = | 0.4–0.6 | 0.40–0.48 |
| $SiO_2/Al_2O_3$ | = | 8–20 | 10–15 |
| $H_2O/Na_2O$ | = | 12–48 | 15–20 |

The reaction mixture is preferably seeded with a slurry comprising 4 to 10 wt %, more preferably 6 to 8 wt. %, of the reaction mixture and having a composition in the following molar ratios:

|  |  | Preferred |
|---|---|---|
| $Na_2O/SiO_2$ | = | 0.8–1.3 |
| $SiO_2/Al_2O_3$ | = | 3–20 |
| $H_2O/Na_2O$ | = | 5–45 |

According to the invention, the substrate to be coated is introduced into the reaction mixture prior to the formation of zeolite Y.

The substrate may be metal or non-metal selected having regard to the intended function of the coated substrate. Thus, the substrate may be, for example, a metal such as aluminium, iron, steel, stainless steel, nickel or titanium, a sintered metal material or a refractory or ceramic material such as a glass, magnesia, alumina, silica or other inorganic oxide, silicate or carbide. The substrate may be in the form of extended bodies such as bars, balls, chains, mesh, plates, sheets, tubes or wires, or in the form of discrete particles. In a preferred aspect this invention relates to forming zeolite coatings on magnetizable substrates, and particularly magnetizable particles, to give a composite product suitable for use as an adsorbent in a magnetically stabilized bed.

The preferred magnetizable particles may be formed of a material which is magnetic in an externally applied magnetic field or magnetic *per se*, and are preferably formed of a ferromagnetic element or compound. These particles should:

(1) not inhibit zeolite formation;
(2) be stable under zeolite preparation conditions;
(3) preferably have a high saturation magnetization to minimise the amount of magnetizable material in the adsorbent. (This criterion could also be met by chemical and/or physical treatment to increase the saturation magnetization of the magnetizable particles—e.g. by chemical reduction to a more highly magnetizable form);
(4) preferably have a high Curie temperature so that the adsorbent may be used in high temperature process;
(5) preferably have a similar thermal expansion behaviour to the zeolite.

Preferred materials are ferromagnetic metals such as iron, cobalt and their alloys such as steels, and ferromagnetic compounds such as magnetite ($Fe_3O_4$). The particles preferably have a mean diameter of greater diameter than 20 Å, more preferably from 100 Å to 200µ, most preferably from 2 to 50µ.

The magnetizable particles are preferably added in an amount of from 0.5 to 90 wt % of the combined weight of reaction mixture plus magnetizable particles, more preferably from 1 to 20 wt % of that combined weight, most preferably 10 to 20 wt %.

The magnetizable particles are added so that zeolite is formed thereon, and it has been found advantageous for the magnetizable particles to be introduced prior to initiating crystallization by heating the reaction mixture.

On heating the reaction mixture containing the magnetizable particles to an appropriate zeolite forming temperature for an appropriate time zeolite is formed on the magnetizable particles resulting in the formation of magnetizable zeolite composites. A wide range of crystallization temperatures and times may be used but, preferably the reaction mixture is heated to from 60° to 120° C. for from 7 to 20 hours.

In a preferred embodiment the reaction mixture containing the magnetizable particles is heated in a rotatable vessel which is rotated about an inclined axis so that as the zeolite is formed it forms a layer on the surface of those particles. The rotation is believed to effect distribution of the particles through the reaction mixture ensuring that substantially the total surface of each particle is exposed to the reaction mixtures so resulting in a more even layer of zeolite formation. The rotational axis of the vessel is inclined to the vertical so that the particles are kept in motion and tumble within the reaction mixture. It is preferred that the particles are alternately lifted out and fall back into the reaction mixture. It is surprising that simply stirring the reaction mixture does not have the same beneficial effect in improving the formation of the zeolite layer on the magnetizable particles—this is thought to be because stirring causes considerable agitation of the reaction mixture giving rise to nucleation centres therein.

The axis of rotation is preferably inclined at an angle of 5° to 90° to the vertical, more preferably at 50° to 80° and most preferably at 60° to 70°. The vessel is preferably rotated at a sufficient speed to ensure mixing of the particles within the reaction mixture by tumbling. Preferably the vessel is rotated at from 5 to 500 rpm, more preferably 10 to 50 rpm.

It is a particularly surprising feature of the invention that the process is capable of forming magnetizable zeolite particles comprising a magnetizable core having a substantially complete layer of zeolite formed therearound. The magnetizable core materals are not zeolitic in structure so that it might be expected that the zeolite would preferentially form separate non-magnetizable zeolite particles rather than form a layer, and it is surprising that the technique of the invention not only brings about formation of a zeolite coating but that this can form a substantially complete layer.

Following formation of the coated substrate the product may be treated to enhance adsorption properties. In particular, a preferred product will comprise in whole or in the major part Na-Y which may be ion exchanged with a solution of a potassium salt, preferably potassium nitrate or chloride, to give the corresponding K-Y product.

The invention extends to a method of separating aromatic hydrocarbons using a magnetically stabilised fluidised bed of adsorbent particles, in which the particles are prepared by the process of the invention.

The process preferably involves providing a bed of magnetizable adsorbent particles which are fluidized by the flow of liquid through the bed; applying a magnetic field to the bed to stabilize the orientation of the bed; adsorbing components of a liquid feedstream of hydrocarbons by passing the feedstream through the bed; and desorbing the adsorbed components with a desorbent. Efficiency of separation of the hydrocarbon components is increased by the use of adsorbent particles which pass through a 40 mesh screen, U.S. Standard, while being able to maintain high liquid velocity (throughput) but without the high pressure drops which hampered previous fixed bed processes.

Once the hydrocarbon component of the feedstock is adsorbed onto the particular adsorbent material, it is removed by the use of a selected desorbent. This desorbent is a material which is capable of displacing the sorbate components of the feedstock material. The desorbent selected may be diluted to obtain the desired strength relative to the hydrocarbon being separated. If the diluent is not adsorbed, then the combined desorbent plus diluent stream is most precisely described as eluent. However, as many nominal diluents may themselves actually serve as extremely weak descorbents, for the purposes of the present invention the combined stream will be referred to as desorbent. For example, the desorbent used in the separation of xylene isomers may be a mixture of toluene and carrier, such as $C_{10}$ to $C_{14}$ linear paraffins; toluene acts by competing with the xylene isomers (or other feed components) for the active sites. Among the suitable desorbents, and particularly useful in the separation of isomeric $C_8$ aromatic hydrocarbons, are toluene, m-diisopropylbenzene, p-diethylbenzene, mixtures of diethylbenzene isomers, o-dichlorobenzene, and the like. This list, of course, is not all encompassing; other desorbents may be selected provided that they are capable of displacing the sorbent components of the feedstock material.

The use of the zeolite composites of the invention in such processes as the adsorbent is advantageous since the composites of the invention provide smaller adsorbent particles than obtained by conventional methods which act as efficient adsorbents and may in a magnetically stabilised bed be used without the pressure drop problems normally associated with small particles. Moreover, the composites of the invention by having the zeolite material as a relatively thin layer over magnetizable particles avoid the drawback of conventional adsorbents where much of the zeolite is trapped within large agglomerate where its adsorbent properties are not utilised.

The following Examples are now given, though only by way of illustration, to show certain aspects of the invention in more detail.

Test Methods: Measurement of Magnetic Yield

To evaluate the products of the process of the invention, test methods were developed to determine the percentage of the adsorbent (zeolite Y) synthesized that was made magnetizable—i.e. that is, the zeolite Y adhering to the magnetizable core particle.

The magnetic yield is defined as:

$$\text{Magnetic yield} = \frac{(\text{wt magnetizable fraction}) - (\text{wt metal in sample})}{(\text{wt total sample}) - (\text{wt metal in sample})} \times 100\%$$

To determine this magnetic yield, it was necessary to be able to separate magnetic and non-magnetic fraction of the products. This was carried out as follows.

Procedure 1 gram of carefully crushed sample and 20 ml acetone were added to a 20 ml sample-tube. The tube was closed and shaken, then a composite of three magnets (Tamson-Alnico N 4005) was place on the bottom of the tube which was subjected to a second shaking. The magnetic particles were attracted by the magnet. The liquid and non-magnetic particles were decanted off.

The same procedure was repeated a second time. Only a minor amount of further non-magnetic particles were removed in the second treatment. Acetone which remained in the tube was soaked up with a dry paper tissue and finally the sample-tube was loosely covered with aluminium foil and dried for 1 hour at 100° C. After cooling for 10–15 minutes at room temperature the magnetic residue was weighed. The magnetic yield was then calculated as described above.

SEM Assessment

The particles produced by the invention were also investigated using scanning electron microscope (SEM) photography. These enabled individual particles to be seen and a visual assessment made of the percentage of the magnetizable particle covered by zeolite to be estimated.

EXAMPLE 1

Preparation of Magnetizable Zeolite Y

A mixture was made of 9.61 g alumina trihydrate and 32.56 g sodium hydroxide in 23.75 g water and 49.99 g of 3–4 micron iron spheres were added. The mixture was stirred for 15 seconds. Then 148.37 g of Ludox HS-40 (a commercially available silica gel) was added and stirring continued for ½ minute. Subsequently, a slurry of amorphous nucleation centres (slurry-composition: $16Na_2O:Al_2O_3:15SiO_2:320H_2O$) was added and stirring was continued for another ½ minute. The resulting gel had the molar composition: $6.9Na_2O:Al_2O_3:16.0SiO_2:115H_2O$.

The entire mixture was placed in a rotatable vessle mounted within an oil bath so that is axis of rotation was at an angle of 60° to the vertical. The vessel was rotated at 25 rpm at 98° C.

74.69 of product was obtained (a yield of 10.9 Na-Y) containing 66.8 wt % Fe and this was analysed by scanning electron microscopy and found to comprise magnetizable particles substantially completely coated with zeolite Y. The magnetic yield of the product was determined as 92%.

COMPARATIVE EXAMPLE 1

To provide a comparison, a similar preparation to Example 1 was carried out in which the reaction mixture of this zeolite crystallization gel and 30 g of 3–4 micron iron particles was heated in a stationary vessel at 97° C. for 16.5 hours, the vessel being simply stirred at 25 rpm. 55.15 g of product was obtained containing 54.4 wt % Fe. This had a magnetic yield of 42% and SEM showed only 25% of the iron particles to be effectively covered with zeolite.

COMPARATIVE EXAMPLE 2

The procedure of Example 1 was again repeated. The zeolite Y forming reaction mixture had the composition: $6.9Na_2O:Al_2O_3:16SiO_2:112H_2O$, and the entire mixture of this zeolite crystallization gel and 30 g of 3–4 micron iron particles was heated in a static crystallization for 16 hours at 98° C. 54.06 g of product was obtained containing 55.5 wt % iron particles. This had a magnetic yield of 43% and SEM showed again only 25% of the iron particles to be covered with zeolite.

The Comparative Examples show that the process of the invention enables a more complete covering of magnetizable particles by a zeolite layer to be achieved.

EXAMPLES 2–3 and COMPARATIVE EXAMPLES 3–4

In Examples 2 and 3 the general procedure outlined in Example 1 was repeated using different magnetizable particles. In Comparative Examples 3 and 4 the stirred synthesis described in Comparative Example 1 was repeated using the magnetizable particles of Examples 2 and 3. The results of all the Examples are given in Table 1 below.

TABLE 1

| Example | Zeolite Reaction mixture - molar composition | Magnetizable Particles amount (g)/ size (micron)/type | Reaction Vessel mixing/speed (rpm) | Product magnetic yield (%) | Surface of particles covered by zeolite (%) |
| --- | --- | --- | --- | --- | --- |
| Example 1 | $6.9Na_2O:Al_2O_3:16.0SiO_2:115H_2O$ | 49.9/3–4/iron | Rotated 25 rpm at | 92 | 100% |

TABLE 1-continued

| Example | Zeolite Reaction mixture - molar composition | Magnetizable Particles amount (g)/ size (micron)/type | Reaction Vessel mixing/speed (rpm) | Product magnetic yield (%) | Surface of particles covered by zeolite (%) |
|---|---|---|---|---|---|
| Comp. Ex. 1 | 6.9Na$_2$O:Al$_2$O$_3$:16.0SiO$_2$:120H$_2$O | 30.0/3–4/iron | 60° to vertical Stirred 25 rpm | 42 | 25% |
| Comp. Ex. 2 | 6.9Na$_2$O:Al$_2$O$_3$:16.0SiO$_2$:112H$_2$O | 30.0/3–4/iron | Static 0 rpm | 43 | 25% |
| Example 2 | 6.9Na$_2$O:Al$_2$O$_3$:16.0SiO$_2$:115H$_2$O | 30.0/10–50/stainless steel | Rotated 25 rpm at 60° to vertical | 12 | 90% |
| Comp. Ex. 3 | 6.9Na$_2$O:Al$_2$O$_3$:16.0SiO$_2$:115H$_2$O | 30.0/10–50/stainless steel | Stirred 25 rpm | 13 | 25% |
| Example 3 | | 50.8/<40/magnetite | Rotated 25 rpm at 60° to vertical | 55 | 100 |
| Comp. Ex. 4 | | 40.0/<40/magnetite | Stirred 25 rpm | 58 | 100 |

We claim:

1. A process for the preparation of a zeolite layer upon a substrate which does not have the same crystalline structure as the zeolite, in which process the substrate is contacted with a reaction mixture for forming a zeolite and the reaction mixture is heated to bring about zeolite formation, in which the substrate is tumbled within the reaction mixture during heating so as to cause zeolite formation preferentially as a layer on the surface of the substrate.

2. A process as claimed in claim 1, in which the substrate is introduced into a rotatable vessel containing a reaction mixture for forming the zeolite, the reaction mixture is heated to form zeolite, and during the heating the vessel is rotated about an axis inclined to the vertical so that zeolite is formed as a layer on the surface of the substrate.

3. A process for the preparation of magnetizable adsorbant particles for use in a magnetically stabilized bed, in which process magnetizable particles are introduced into a rotatable vessel containing a reaction mixture for forming a zeolite, the reaction mixture is heated to bring about zeolite formation, and during the heating the vessel is rotated about an inclined axis so that the zeolite is formed as a layer on the surface of the magnetizable particles.

4. A process for the preparation of magnetizable particles comprising zeolite Y for use in a magnetically stabilized bed, in which process magnetizable particles are introduced into a rotatable vessel containing a reaction mixture for forming zeolite Y, the reaction mixture is heated to form zeolite Y, and during the heating the vessel is rotated about an inclined axis so that zeolite Y is formed as a layer on the surface of the magnetizable particles.

5. A process as claimed in claim 4, in which the reaction mixture is an aqueous composition comprising sodium, silica, alumina and water in the following ratios, expressed in terms of mole ratios of oxides:

| Na$_2$O/SiO$_2$ | = | 0.38–0.60 |
|---|---|---|
| SiO$_2$/Al$_2$O$_3$ | = | 8–20 |
| H$_2$O/Na$_2$O | = | 12–48. |

6. A process as claimed in claim 5, in which the reaction mixture comprises reactants in the following molar ratios, expressed in terms of oxides:

| Na$_2$O/SiO$_2$ | = | 0.40–0.48 |
|---|---|---|
| SiO$_2$/Al$_2$O$_3$ | = | 10–15 |
| H$_2$O/Na$_2$O | = | 15–20. |

7. A process as claimed in claim 4 in which the reaction mixture is seeded with a slurry comprising 4 to 10 wt % of the reaction mixture and having a composition in the following molar ratios:

| Na$_2$O/SiO$_2$ | = | 0.8–13 |
|---|---|---|
| SiO$_2$/Al$_2$O$_3$ | = | 3–20 |
| H$_2$O/Na$_2$O | = | 5–45. |

8. A process as claimed in claim 4, in which the magnetizable particles are particles of iron, cobalt, steel or magnetite.

9. A process as claimed in claim 4, in which the particles have a mean diameter of from 2 to 50 microns.

10. A process as claimed in claim 4, in which the rection mixture contains from 1 to 20 wt % of magnetizable particles.

11. A process as claimed in claim 4, in which the formed magnetizable zeolite particles comprise the sodium form of zeolite Y which is thereafter ion exchanged with a solution of a potassium salt to form the corresponding potassium form of zeolite Y.

12. A process as claimed in claim 2, in which the vessel is rotated about an axis inclined at an angle of from 30° to 85° to the vertical.

13. A process as claimed in claim 12, in which the axis of rotation is at an angle of 50° to 80° to the vertical.

14. A process as claimed in claim 2, in which the speed of rotation of the vessel is from 5 to 500 rpm.

15. A process as claimed in any one of claims 3 to 14, in which the zeolite is formed as a substantially complete layer around the magnetizable particles.

* * * * *